(12) United States Patent
Feinberg et al.

(10) Patent No.: US 10,241,179 B2
(45) Date of Patent: Mar. 26, 2019

(54) CINE PHASE CONTRAST SIMULTANEOUS MULTI-SLICE AND MULTI-SLAB IMAGING OF BLOOD FLOW AND CEREBROSPINAL FLUID MOTION

(71) Applicants: David Feinberg, Sebastapol, CA (US); Liyong Chen, China (CI)

(72) Inventors: David Feinberg, Sebastapol, CA (US); Liyong Chen, China (CI)

(73) Assignee: ADVANCED MRI TECHNOLOGIES, LLC, Sebastopol, CA (US)

(*) Notice: Subject to any disclaimer, the term of this patent is extended or adjusted under 35 U.S.C. 154(b) by 164 days.

(21) Appl. No.: 15/469,043

(22) Filed: Mar. 24, 2017

(65) Prior Publication Data

US 2018/0275237 A1    Sep. 27, 2018

Related U.S. Application Data

(60) Provisional application No. 62/468,667, filed on Mar. 8, 2017.

(51) Int. Cl.
| | |
|---|---|
| *G01R 33/563* | (2006.01) |
| *G01R 33/46* | (2006.01) |
| *G01R 33/483* | (2006.01) |
| *A61B 5/055* | (2006.01) |
| *A61B 5/00* | (2006.01) |
| *A61B 5/145* | (2006.01) |

(52) U.S. Cl.
CPC ........ *G01R 33/56325* (2013.01); *A61B 5/055* (2013.01); *A61B 5/14507* (2013.01); *A61B 5/4076* (2013.01); *G01R 33/4633* (2013.01); *G01R 33/4835* (2013.01); *G01R 33/56316* (2013.01); *G01R 33/56308* (2013.01)

(58) Field of Classification Search
CPC .......... G01R 33/56325; G01R 33/4633; G01R 33/4835; G01R 33/56316; G01R 33/56308
See application file for complete search history.

(56) References Cited

U.S. PATENT DOCUMENTS

| | | | | |
|---|---|---|---|---|
| 2015/0276901 A1* | 10/2015 | Cowan | ............... | G01R 33/5659 324/309 |
| 2016/0128592 A1* | 5/2016 | Rosen | ................ | A61B 5/04012 600/411 |
| 2016/0341807 A1* | 11/2016 | Bilgic | ................ | G01R 33/4835 |

* cited by examiner

*Primary Examiner* — Gregory H Curran
(74) *Attorney, Agent, or Firm* — Cooper & Dunham LLP (57) ABSTRACT

An MRI method and an MRI system that simultaneously detect blood and/or CSF velocity or flow in plural slices or slabs preferably as not spatially adjacent. Two or more sets of interleaved slices or slabs can be assembled to cover the desired volume and derive higher quality MRI signals and images without a need for a contrast agent, even where the volume is too large for effective flow imaging with known techniques without contrast agent.

20 Claims, 5 Drawing Sheets

CINE PHASE CONTRAST SIMULTANEOUS MULTI-SLICE AND MULTI-SLAB IMAGING OF BLOOD FLOW AND CEREBROSPINAL FLUID MOTION

REFERENCE TO RELATED APPLICATION

This patent application claims the benefit of U.S. Provisional patent application 62/468,667 filed Mar. 8, 2017, and hereby incorporates by reference its entire contents.

FIELD

This patent specification relates to magnetic resonance imaging (MRI).

BACKGROUND

This patent specification refers to, and hereby incorporates by reference, the items listed at the end and identified by reference (ref) numbers in parenthesis in the discussion below.

Phase contrast imaging is a magnetic resonance imaging (MRI) technique that can be used to visualize moving fluid. It is typically used for MR angiolgraphy that does not require introducing a contrast agent in the subject. Phase contrast imaging relies on the assumption that spins that are moving in the same direction as a magnetic field gradient develop a phase shift that that is proportional to the velocity of the spins. In principle, bipolar gradients (two gradients with equal magnitude but opposite direction) are used to encode the velocity of the spins. Stationary spins undergo no net change in phase after the two gradients are applied, but moving spins experience a different magnitude in phase response to the second gradient compared with the first. The detected net phase shift can be used to calculate the velocity of the spins, or an image obtained with a bipolar gradient can be subtracted from an image of the same slice obtained without using a bipolar gradient to thereby determine velocity from net phase shift and highlight flow. Gradient moment nulling can be used to balance the phase of all gradient pulses to achieve only velocity phase shifts in the echo signal from an effective bipolar pulse.

The most common and available method for hemodynamic MR velocity imaging on commercial clinical scanners is believed to be two-dimensional (2D) phase contrast (PC) imaging using a bipolar gradient pulse (ref 1) to encode the signal phase with velocity in cine gradient echo (GRE) sequences with low flip angle radio frequency (RF) pulses, and cardiac gating (cine-PC) through the cardiac cycle (ref 1, ref 2). Cine-PC 2D imaging measures flow velocity in a single slice plane and scan time is increased proportional to the number of repeated slice planes through arteries or cerebrospinal fluid (CSF) passageways.

SUMMARY OF THE DISCLOSURE

This patent specification describes an MRI method and an MRI system that use a new approach involving essentially simultaneously detecting blood and/or cerebral spinal fluid (CSF) velocity or flow in plural 2D slices or plural 3D slabs of the subject. The slices or slabs preferably as not spatially adjacent but two or more sets of interleaved slices or slabs can be taken and the resulting images assembled to cover an entire region of interest such as the brain. This greatly speeds up detecting and imaging flow and provides the clinician with information not available from the known conventional approach.

This new approach makes use of the discovery that the combination of (i) simultaneous 2D multi-slice (SMS) or simultaneous multiple 3D volume slabs (SMV) imaging referred to as SMV MR 4D Flow imaging with (ii) blood velocity measurement by adding bipolar gradient pulses to achieve phase contrast imaging (PC), has unexpected and great advantages over single-slice or single-slab PC (ref 2) or 4D PC imaging techniques (ref 4) including FLASH, other gradient echo sequences, spiral trajectory, radial trajectory, EPI, TSE, and RARE techniques. The inventors have discovered that with the new approach, the physiological variations between heart cycles in cardiac pulsations in arterial blood flow do not introduce differences in velocity measurements when the imaged slices or slabs are acquired at the same time. The inventors also have discovered that in conventional 3D slab imaging there is a limit to the distance traveled by inflow of fully relaxed magnetization from unexcited (or unlabeled) spins when the spin's pathway in the 3D volume is too large in the direction of inflow. As a consequence of either the velocity being too low or the slab being too thick, the branched vessels in the downstream regions of the body in the distal imaging slab may show a lack of signal, which is artifact. This can degrade the accuracy of measuring velocity and blood flow. However, in the new approach the simultaneous multi-slab imaging with gaps of non-excitation between the slabs eliminates or at least substantially reduces this artifactual lack of blood flow because there is a shorter distance for the blood to flow from the adjacent gap regions during image acquisition and there is reduced distance to travel within each slab when the slab is thinner. The complete coverage of a continuous or contiguous region of the body and vessel is achieved by repeating the simultaneous multi-slab (SMV) acquisition, offset spatially to cover the previous gap regions.

An important unexpected improvement of flow imaging using the new technique is that flow in thicker slabs or volumes can be imaged well without contrast agents. This is particularly valuable because intravenous contrast agent can be a safety risk and may not be able to be used in patients who have compromised renal systems and are even at risk of renal failure from the contrast agent. With the new method of simultaneous imaging, there is greater inflow of unsaturated spins into the volume undergoing repeated excitation and this makes the use of contrast agent unnecessary. There is a common practice of using gadolinium-based contrast agents injected intravenously to increase the signal recovery in the images The contrast agent shortens T1 of blood and thus allows faster signal recovery and allows blood within the slab to recover signal. The use of gadolinium will not be necessary if blood spins are entering the slab from adjacent unexcited areas between the slices or slabs according to the new approach described in this patent specification. Second, these spins entering a thinner slab travel a shorter distance to fill even the distal regions of the thinner slabs. The combined spacing between slabs and use of thinner 3D volume instead of a single thicker 3D volume (slab) allows inflow of spins to reach all areas of the imaged volume. The spins contribute a stronger signal in areas of the image accomplished by using multiple simultaneous thinner slabs instead of a single thicker slab.

The slabs measured in the two or more image acquisitions can partially overlap spatially, and the MRI signals or image portions for overlapped regions can be blended or one of the duplicated signals or image portions can be discarded. This can eliminate or mostly eliminate artifactual signal loss at the slab edge due to selective excitation imperfections that define the slab profile.

The inventors have further discovered that the MRI signal loss in vessel and body organ regions from motion artifacts is reduced in the new approach. There is a reduction in scan time when acquiring multiple slices using time sequential signals from each respective slice is replaced by much faster simultaneous slice and simultaneous slab acquisitions.

The inventors realized that simultaneous recording of slices or slabs with spaces or gaps is useful for measuring flow and velocity in different vessel regions and organs that may have disease, or measuring CSF velocity in different spinal and cerebral CSF passageways. In some cases it will be more time-efficient to acquire a set of simultaneous slices or simultaneous slabs without repeating a second set to completely cover all regions of organs and of vessels. There is a great increase in imaging speed and improvement in reducing errors due to variations in heart rate and breathing using simultaneous slice phase contrast imaging compared to current existing single-slice phase contrast imaging which is lengthened in time proportional to acquiring more slices.

In the new approach, the unique combination of three processes: 1) velocity phase encoding with bipolar gradient pulses, 2) simultaneous slice or simultaneous slab acquisition utilizing multi-band RF excitation pulses, and 3) utilization of spatial separation between the slices or slabs to optimally allow greater blood inflow into the 2D or 3D image, creates: i) much higher imaging speed and image quality in blood velocity and blood flow images compared with known conventional approaches, ii) an ability to reduce or eliminate cardiac cycle variation dependent artifacts, iii) reduction in artifacts related to poor blood filling of vessels during image acquisition, and iv) images from fewer MR signals by acquiring combined simultaneous signals and thus obtaining higher spatial resolution of blood flow in reduced scan times.

BRIEF DESCRIPTION OF THE DRAWINGS

FIG. 4a illustrates conventional imaging of a thick 3D slab. During the TR between excitations, unsaturated spins move into the region between excitations to partially fill vessels reaching proximal (PV) vessel segments but not reaching distal (DV) segments.

DETAILED DESCRIPTION OF PREFERRED EMBODIMENTS

A detailed description of examples of preferred embodiments is provided below. While several embodiments are described, the new subject matter in this patent specification is not limited to any one embodiment or combination of embodiments described herein but encompasses numerous alternatives, modifications, and equivalents. While numerous specific details are set forth in the following description to provide a thorough understanding, some embodiments can be practiced without some or all these details. For clarity, certain technical material that is known in the related art has not been described in detail to avoid unnecessarily obscuring the new subject matter described herein. Individual features of one or several of the specific embodiments described herein can be used in combination with features or other described embodiments. Further, like reference numbers and designations in the various drawings indicate like elements.

Figure 1:
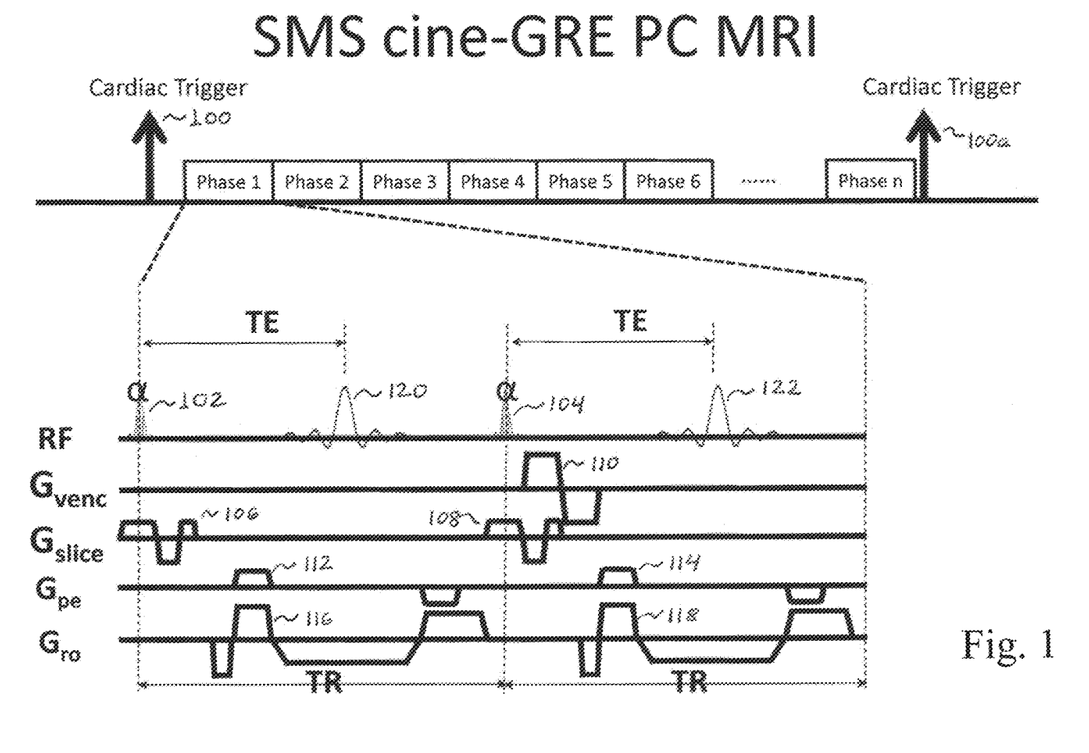
FIG. 1 illustrates a SMS gradient echo Cine-PC pulse sequence where the first multibanded RF pulse in a first TE excites with no velocity sensitization but the second RF pulse sequence in a second TE has bipolar gradients designated as $G_{venc}$ pulse (which can be used on any of the three gradient axes (x,y,z) (ref 4) to give velocity dependent phase shift. Each excitation multiband RF pulse is with phase cycling for controlled aliasing across different k-space data acquisition signals.

FIG. 1 illustrates a non-limiting example of simultaneous detection of MR signals for blood and/or CSF flow from plural slices or slabs, such as four slices or slabs (although there can be fewer or more slices or slabs). An otherwise conventional pulse sequence such a 2D FLASH as used in Siemens MRI scanners (or similar sequences used in MRI scanners by other manufacturers, such as SPGR by GE or CE-FFE-T1 by Philips), can be used with cine acquisition and prospective cardiac gating to excite plural slices or slabs in a subject with multiband (MB) radio frequency (RF) pulses and a bipolar velocity gradient. Each RF pulse in this example consists of a superposition of four frequency bands that are slightly offset in frequency from each other. Referring to FIG. 1, the sequence starts with a cardiac pulse gating or trigger 100 that can come from cardiac gating, e.g., upon a selected point of the subject's cardiac cycle. In the illustrated Phase 1 of the sequence, two multi-band pulses 102 and 104, spaced in time, are applied to a subject in an MRI scanner. Each RF pulse contains four frequency bands and excites four slices (or slabs) that are defined by two respective slice select gradients 106 and 108 on a $G_{slice}$ axis. Concurrently with the gradient 108, but not gradient 106, a velocity encode gradient 110 is applied to the subject on a $G_{venc}$ axis. Phase encode pulses 112 and 114 shown on a $G_{pe}$ axis are applied. Readout gradients 116 and 118 shown on a $G_{ro}$ axis are applied, timed relative to the RF pulses so that MR signals 120 and 122 can be detected with a suitable multi-coil array antenna, after a time interval TE from RF pulses 102 and 104 respectively. Phase 1 is followed in time by an otherwise same Phase 2, then Phase 3, . . . , and Phase n (where n is a positive integer) and the resulting MR signals from these phases are combined to reduce noise and otherwise improve signal quality. The MR signal 120 as combined for phases 1-n can be used to reconstruct static MR images of the four slices or slabs that do not highlight blood or CSF flow, and MR signal 122 as combined for phases 1-n can be used as a measure of flow and/or to reconstruct MR images of the same four slices or slabs that show blood and/or CSF flow. The two sets of MRI signals or images can be subtracted to highlight only velocity dependent phase shift. Controlled aliasing can be used to improve the images. Upon another cardiac trigger or gating pulse 100a, another sequence of phases 1-n can start that can be with gradients oriented to detect flow in the same direction or in another selected direction relative to the subject.

The four slices (or some other number of slices) can be thin, essentially planar slices, or they can be thicker such that they are 3D slabs of the subject. An important additional feature of the new approach this patent specification describes is to make the slice select gradients 106, 108 sufficiently wide to select 3D slabs of tissue rather than thin, essentially 2D slices. The additional application of acquisition cycles in which a second phase encoding gradient pulse is incrementally or otherwise changed in amplitude results in a 3D spatial k-space data set which gives 3D spatial map with FT reconstruction.

Figure 2:
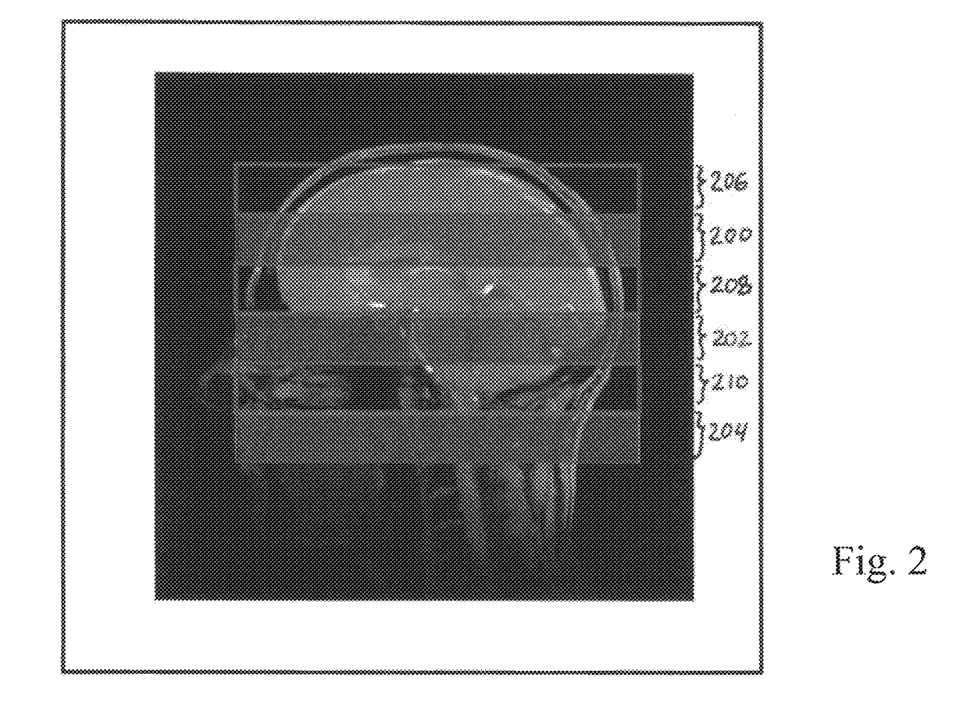
FIG. 2 illustrates a scout view of two interleaved sets of images, where each set consists of images of 3 slabs, with 100% slab spacing, and the two sets are imaged in succession using SMS Cine-PC pulse sequence.

FIG. 2 illustrates an example or interleaved slabs of a subject's brain in sagittal view. In this case three rather than four slices or slabs are simultaneously excited with RF pulses each consisting of three frequency bands with offsets between them. The slice select gradients 106, 108 are sufficiently wide in this case to select a set of 3D slabs 200, 202, and 204 for a first sequence of phases 1-n of the type illustrated in FIG. 1. Notably, these three slabs are not contiguous but are vertically spaced from each other. A first pulse sequence such as illustrated in FIG. 1 produces MR signals 120 and 122 for slabs 200, 202, and 204, for phases 1-n. A subsequent pulse sequence can be otherwise the same but with RF pulses 102, 104 and slice select gradients 106, 108 that select a second set of slabs, namely slabs 206, 208, and 210 that are spatially interleaved with slabs 200, 202, and 204. The slabs of the two sets preferably slightly overlap, but can be contiguous or even somewhat spaced from each other. The MR signals obtained from the two pulse sequences and the two sets of slabs thus can cover substantially the entire brain as evident from the sagittal view of the subject's head. In other examples, a different number of interleaved slabs can be excited, or they can cover a different part of the subject's body such as some or all of the chest or abdomen The slab images reconstructed from the two sets of slabs can be interleaved into an MR image of the entire brain (or other body part of interest). As noted above, if the slabs overlap, the overlap regions can be used to improve the image and reduce or eliminate artifacts due to imperfect slice edge definition. For example, the information from the two overlapped regions of the sets of acquisitions (for the two sets of slabs) can be combined, such as by adding and dividing by two, or by a factor that varies with position in the overlapped region. The image can be reconstructed from MR signals 122 only (showing blood and/or CSF flow), or from MRI signals 120 only (static image), or from both, and can include a subtraction or other combination of the MR signals 120 and 122 or the images reconstructed from those MRI signals.

As one example of implementation using an MRI system such as currently commercially available from Siemens or GE, controlled aliasing (ref 3) with FOV/3 shift can be performed with phase cycling the multi-band (MB) RF pulse, for 3 slices (0,0,0), (0,120,240), (0,240,120), on the k-space PE axis. Imaging can be performed in normal subjects with both single-slice cine-GRE PC and SMS cine-GRE PC for blood velocity in 32-channel head coil and CSF velocity imaging in 12-channel coil. Imaging parameters for cine-PC 2D SMS=1-4 and GRE cine-PC can be: SMS=1-4, TR=8.4 ms, TE=4.65 ms, BW=280 Hz/pixel, FA($\alpha$)=15°, IPAT=2, FOV=192×192 mm2, matrix=(128× 128) or (256×256), in-plane resolution (res)=(0.75×0.75) or (1.5×1.5) mm2, venc=80 cm/s, with 16 mm or 32 mm slice spacing and slice thickness=4 mm. Imaging by combining head-neck-spine coil array with head (12ch), neck (12ch) spine (4ch), can be performed with SMS-3, res=1.25 mm, slice=5 mm, venc=100 cm/s, TR=9.55 ms, TE=5.8 ms, FA ($\alpha$)=15°. The preparation time for spatial sensitivity data, single band and dummy scans can be short, about 180 ms. Through plane velocities can be measured with $G_{venc}$ on G-slice axis as illustrated in FIG. 1. The velocity phase shifts are positive (white) and negative (black) corresponding to superior cranial and inferior caudal directions, respectively. The resulting reconstructed images would show a reduction in slice cross-talk artifacts achieved with use of controlled aliasing as seen by comparing the averaged phase map of cine-data (arteries—white, vein—black). The total scan time for 2 to 4 slices using SMS2-SMS4 can be 2.2 minutes and similar for conventional single-slice (sms1). There would be no loss, or at most negligible loss, in spatial resolution using SMS acquisitions.

An important gain in signal encoding efficiency with SMS cine-PC stems from the fact that there is no inherent SNR loss from the square root of the reduced data, as occurs with in-plane parallel imaging accelerations. Consequently, plural (n) slices or slabs can be acquired in the time of conventionally acquired single-slice or single-slab cine-PC without SNR reduction other than possible reconstruction noise (g-factor). Hence, SMS velocity phase images acquired with the new approach improve SNR efficiency by as much as square root or N (the number of slices or slabs) over single slice acquisition with no spatial resolution or artifact penalties.

The new technique disclosed in this patent specification, SMS cine-PC, overcomes scan time limitations in acquiring multiple slices with 2D cine-PC imaging. By providing several simultaneous cross-sectional measurements of hemodynamics in vessels or CSF in passageways, SMS cine-PC increases utility of the results for medical diagnosis and treatment of conditions such as hydrocephalus and cardiovascular disease.

In addition, as noted above, because of the use of interleaved slices or slabs, flow in thicker volumes can be assessed or imaged better that with known single-slab or single-volume acquisition. For example, a chest region that is 20 cm thick in the head-toe direction can be assessed or imaged using the new approach with better MRI signals and/or image quality than with the use of the known conventional techniques, and without requiring contrast agent such as gadolinium, particularly for smaller vessels.

Figure 3:
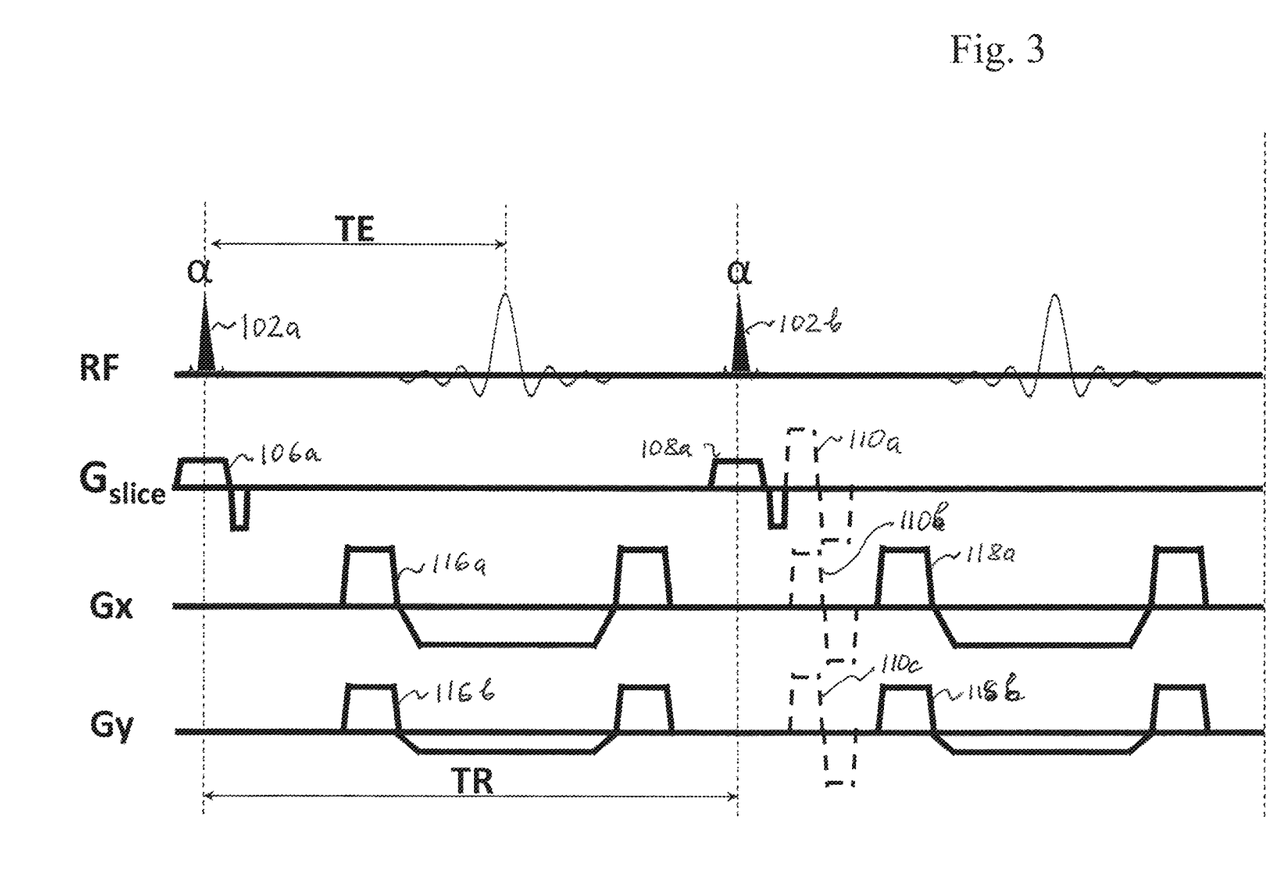
FIG. 3 illustrates an SMS radial Cine-PC pulse sequence where a first multibanded, slice/slab selective RF pulse with flip angle (α) that excites with no velocity sensitization and a second α RF pulse has bipolar gradients that gives velocity-dependent phase shift. The excitation multiband RF pulses (blue) can be with phase cycling for controlled aliasing across different rays. Bipolar gradients on a $G_{slice}$ axis are shown. Velocities in different (X, Y) directions can be used, as illustrated in dash line gradients on the $G_x$ and $G_y$ axes.

FIG. 3 illustrates SMS Cine-PC pulse sequence that is otherwise similar to that of FIG. 1 but is for radial imaging (ref 5) and shows a bipolar gradient 110a on the $G_{slice}$ axis and possible bipolar gradients 110b and 110c on the Gx and Gy axes, and readout gradients 116a, 116b, 118a, and 118b. A first multibanded slab-selective RF pulse 102a excites with no velocity sensitization and a second RF slab selective pulse 102b has a bipolar gradient to give velocity-dependent phase shift. The excitation multiband RF pulses use phase cycling for controlled aliasing across different rays (ref 5). One, two, or all three of the bipolar gradient can be used, depending on which direction of flow is of interest in a given MRI signal acquisition.

Figure 4A:
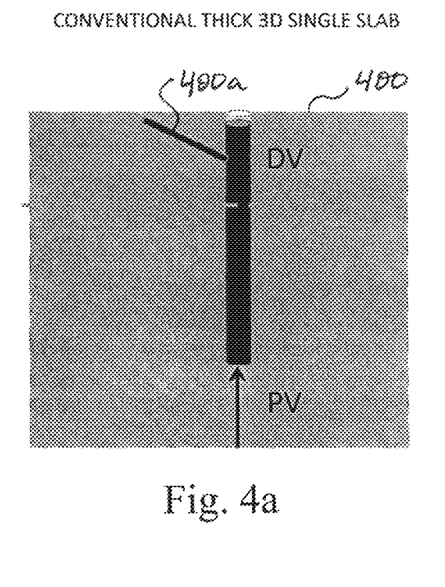
Figure 4B:
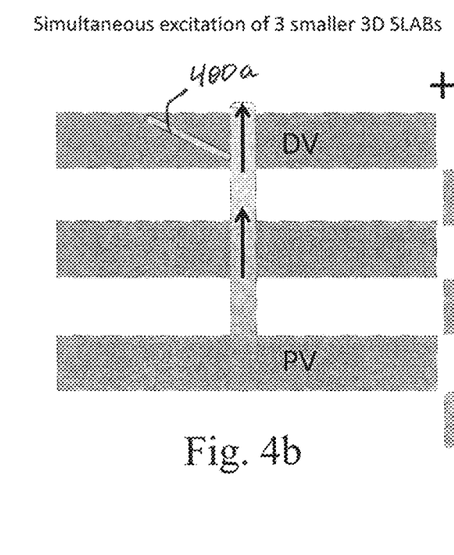
FIG. 4b illustrates simultaneous excitation of three thinner slabs with gap regions between them, allowing spins to move into more distal regions of the vessels, in an example of the new approach described in this patent specification.
Figure 4C:
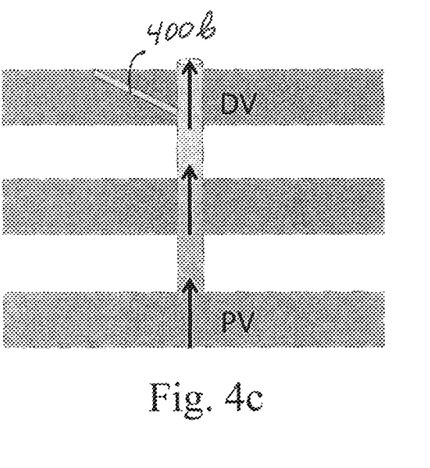
FIG. 4c illustrates repeating the imaging of FIG. 4b but with the slab regions repositioned between those of FIG. 4b, so the MRI signals or images of the two sets of slabs can be combined to give complete coverage of the region defined by the six slabs.

FIGS. 4a, 4b, and 4c illustrate an example of this benefit of the new approach. FIG. 4s shows a thick slab or volume 400 of patient tissue that has blood vessels including in a proximal vessel segment labeled PV and a distal vessel segment labeled DV. A relatively small branch vessel 400 a is in segment 4V During periods TR between excitation with an RF pulse (see FIG. 1), unsaturated spins move in the vertical up direction to partially fill vessels, reaching the PV segments but few if any reach the DV segment. The result is that flow in the vessels in the DV segment are not imaged or at least are not imaged well. FIGS. 4b and 4c illustrate how a comparable thicker slab or volume can be imaged well using the new approach this patent specification describes. The volume is divided into two sets each made of three thinner slabs. In a first sequence of phases 1-n, three slabs with gaps between them are imaged using the new approach, as seen in FIG. 4b. Each slab in FIG. 4b is much thinner that the slab or volume 400 of FIG. 4a so during the TR periods the spins can fill the vessels in each of the three slabs, including the branch vessel 400a. FIG. 4c illustrates repeating the scan for another three slabs, one of which includes another branch vessel 400b. that are in the gaps not images in the sequence that images the slabs of FIG. 4b. The MRI signals from the slabs of FIGS. 4b and 4c now cover the entire region that is comparable in thickness with the region of FIG. 4a, and the branch vessels are imaged better because the spins fill them. As one example, a chest region that is 20 cm thick would not produce good quality MRI signals for flow in a chest volume 20 cm thick, at least for a region such as the one labeled DV in FIG. 4a, but imaging with the new approach would.

Figure 5:
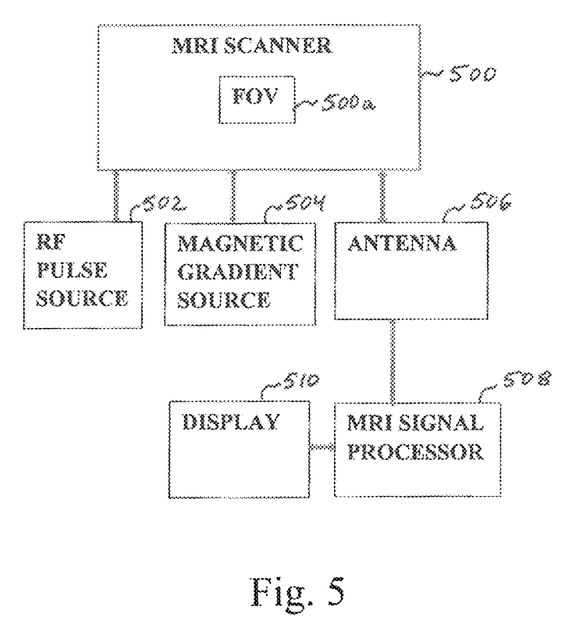
FIG. 5 is a block diagram illustrating a system implementing an example of the new approach described in this patent specification.

FIG. 5 illustrates a system implementing an example of the new approach described in this patent specification. A CT scanner 500, such as a current generation scanner commercially available from companies such as Siemens, GE, Philips, and others, has a field-of-view (FOV) region 500a in which a subject to be imaged is positioned. An RF pulse source 502 supplies the multi-band RF signals discussed above for FIGS. 1 and 3, a magnetic gradient source 504 supplies the gradients discussed for FIGS. 1 and 3, and an antenna 506 acquires the MRI signals also discussed for FIGS. 1 and 3. An MRI signal processor 508 processes the MRI signals as discussed above to detect blood and/or CSF in the imaged slices or slabs in the FOV, and supplies the results to display 510, to show for example an image such as in FIG. 2 but with flow highlighted or to show other indications of flow.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

REFERENCES

1. Hahn E L, Detection of Sea-Water Motion by Nuclear Precession, J Geophys Res, Vol 65, No. 2, 776-777 (February 1960)
2. Enzmann D R, et al., Cerebrospinal Fluid Flow Measured by Phase-Contrast Cine MR, AJNR:14 1301-1307 (November-December 1993)
3. Breuer F A, et al., Controlled Aliasing in Parallel Imaging Results in Higher Acceleration (CAIPARINHA) for Multi-Slice Imaging, MRM 53:684-691 (2005)
4. Markl M, et al., 4D Flow MRI, JMRI 36:1015-1036 (2012)
5. Block K T, et al., Undersampled Radial MRI with Multiple Coils. Iterative Image Reconstruction Using a Total Variation Constraint, MRM 57:1086-1098 (2007).

What it claimed is:

1. A magnetic resonance imaging (MRI) method that essentially simultaneously detects blood flow and/or cerebrospinal fluid (CSF) movement in a first set of plural slices or slabs of a subject in an MRI scanner and then in a second set of slices of slabs interleaved with those of the first set to thereby cover a volume of the subject, which method includes:
    applying, to the subject in the MRI scanner, in each of a time succession of phases, a first radio frequency (RF) excitation pulse and a second RF excitation pulse;
    wherein:
        each of the RF pulses is a multi-band pulse that includes plural frequency bands selectively offset from each other in frequency and/or phase; and
        the frequency bands in each of the multi-band pulses essentially simultaneously excite a first set of respective spaced-apart plural slices or slabs in the subject, thereby causing the subject to essentially simultaneously emit MRI signals from each of the slices or slabs;
    applying to the subject in the MRI scanner, in a timed relationship relative to each of the RF pulses:
        slice encode magnetic gradients $G_{slice}$
        phase encode magnetic gradients $G_{pe}$; and
        readout magnetic gradients $G_{ro}$;
    applying to the subject, in timed relationship only to each second RF pulse, a bipolar velocity encoding magnetic gradients $G_{venc}$;
    acquiring the MRI signals emitted from the subject with an antenna device in timed relationship to the readout magnetic gradients $G_{ro}$;
    repeating the applying and acquiring steps for a second set of respective spaced-apart plural slices or slabs in the subject interleaved with the slices or slabs of the first set to thereby cover a volume of the subject;
    computer-processing the acquired MRI signals into indications of at least one of blood flow and cerebrospinal fluid (CSF) movement in the slices or slabs; and
    displaying said indications.

2. The MRI method of claim 1, including selecting a direction relative to the subject along which the bipolar velocity encoding magnetic gradient is applied.

3. The MRI method of claim 1, in which at least some of the slices or slabs of the first set partly overlap with slices or slabs of the second set.

4. The MRI method of claim 3, including computer-processing the MRI signals for regions where the first and second set of slices or slabs overlap by blending the signals from the two sets for the overlapped regions to thereby enhance a quality of the signals from said regions.

5. The MRI method of claim 1, in which said slices or slabs are sufficiently thin for unsaturated spins entering one side of each slice or slab to reach the opposite side and thus produce sufficient MRI signals for detecting flow in smaller vessels throughout each slice or slab.

6. The MRI method of claim 1, including applying radial imaging of flow.

7. A magnetic resonance imaging (MRI) method that essentially simultaneously detects blood flow and/or cerebrospinal fluid (CSF) movement in plural slices or slabs of a subject in an MRI scanner, which method includes:
  applying, to the subject in the MRI scanner, in each of a time succession of phases, a first radio frequency (RF) excitation pulse and a second RF excitation pulse; wherein:
    each of the RF pulses is a multi-band pulse that includes plural frequency bands selectively offset from each other in frequency and/or phase; and
    the frequency bands in each of the multi-band pulses essentially simultaneously excite a first set of respective spaced-apart plural slices or slabs in the subject, thereby causing the subject to essentially simultaneously emit MRI signals from each of the slices or slabs;
  applying to the subject in the MRI scanner, in a timed relationship relative to each of the RF pulses:
    slice encode magnetic gradients $G_{slice}$
    phase encode magnetic gradients $G_{pe}$; and
    readout magnetic gradients $G_{ro}$;
  applying to the subject, in timed relationship only to each second RF pulse, a bipolar velocity encoding magnetic gradients $G_{venc}$;
  acquiring the MRI signals emitted from the subject with an antenna device in timed relationship to the readout magnetic gradients $G_{ro}$;
  computer-processing the MRI signals acquired with the antenna device into indications of at least one of blood flow and cerebrospinal fluid (CSF) movement in the slices or slabs; and
  displaying said indications.

8. The MRI method of claim 7, including selecting a direction relative to the subject along which the bipolar velocity encoding magnetic gradient is applied.

9. The MRI method of claim 7, further including repeating the applying, acquiring, and computer-processing step for a second set of slices or slabs interleaved with the first set, wherein the first and second set occupy a volume of the subject, and displaying said indications for the entire volume.

10. The MRI method of claim 9, in which at least some of the slices or slabs of the first set partly overlap with slices or slabs of the second set.

11. The MRI method of claim 10, including computer-processing the MRI signals for regions where the first and second set of slices or slabs overlap by blending the signals from the two sets for the overlapped regions to thereby enhance a quality of the signals from said regions.

12. The MRI method of claim 7, in which said slices or slabs are sufficiently thin for unsaturated spins entering one side of each slice or slab to reach the opposite side and thus produce sufficient MRI signals for detecting flow in smaller vessels throughout each slice or slab.

13. The MRI method of claim 7, including applying radial imaging of flow.

14. A magnetic resonance imaging (MRI) system comprising:
  an MRI scanned having a field of view FOV);
  a source of radio frequency pulses applying to the FOV, in each of a time succession of phases, a first radio frequency (RF) excitation pulse and a second RF excitation pulse, wherein each of the RF pulses is a multi-band pulse that includes plural frequency bands selectively offset from each other in frequency and/or phase, and the frequency bands in each of the multi-band pulses essentially simultaneously excite a first set of respective spaced-apart plural slices or slabs of the subject in the FOV, thereby causing the subject to essentially simultaneously emit MRI signals from each of the slices or slabs;
  a source of magnetic gradients applying to the subject in the FOV, in a timed relationship relative to each of the RF pulses, slice encode magnetic gradients $G_{slice}$, phase encode magnetic gradients $G_{pe}$, and readout magnetic gradients $G_{ro}$;
  said source of magnetic gradients being further configured to apply to the subject in the FOV, in timed relationship only to each second RF pulse, a bipolar velocity encoding magnetic gradients $G_{venc}$;
  an antenna detecting the MRI signals emitted from the subject in the FOV in timed relationship to the readout magnetic gradients $G_{ro}$;
  a processor configured to computer-process the MRI signals detected with the antenna into indications of at least one of blood flow and cerebrospinal fluid (CSF) movement in the slices or slabs; and
  a computer display displaying said indications.

15. The MRI system of claim 7, wherein said source of bipolar velocity encoding gradient in a selectable direction relative to the subject.

16. The MRI system of claim 7, wherein the system is configured to additionally detect MRI signals for a second set of slices or slabs interleaved with the first, wherein the first and second set occupy a volume of the subject, and to display said indications for the entire volume.

17. The MRI system of claim 9, in which at least some of the slices or slabs of the first set partly overlap with slices or slabs of the second set.

18. The MRI system of claim 10, in which the computer-processing for regions where the first and second set of slices or slabs overlap comprises blending the signals from the two sets for the overlapped regions to thereby enhance a quality of the signals from said regions.

19. A magnetic resonance imaging (MRI) method that essentially simultaneously detects blood flow and/or cerebrospinal fluid (CSF) movement in plural slices or slabs of a subject in an MRI scanner, which method includes:
  applying, to the subject in the MRI scanner, in each period of a time succession of periods 1 through n, where n is a positive integer greater than unity, one or more radio frequency (RF) excitation pulses, wherein:
    each RF pulses is a multi-band pulse that includes plural frequency bands selectively offset from each other in frequency and/or phase; and
    the frequency bands in each of the multi-band pulses essentially simultaneously excite respective plural slices or slabs in the subject, thereby causing the subject to essentially simultaneously emit MRI signals from each of the slices or slabs;
  applying to the subject in the MRI scanner, in a timed relationship relative to each RF pulse:
    slice or slab encode magnetic gradients $G_{slice}$
    phase encode magnetic gradients $G_{pe}$; and
    readout magnetic gradients $G_{ro}$;
  acquiring the MRI signals emitted from the subject with an antenna device in timed relationship to the readout magnetic gradients $G_{ro}$;
  repeating the applying and acquiring steps for said succession of time periods;
  applying, in at least some of the time periods, one or more bipolar velocity encoding magnetic gradients $G_{venc}$ at one or more selected axes relative to the scanner and in timed relationship with one or more of the RF pulses;

computer-processing the acquired MRI signals, including velocity dependent phase shifts reflected in the MRI signals, into indications of at least one of blood flow and cerebrospinal fluid (CSF) movement in the slices or slabs; and displaying said indications.

20. A magnetic resonance imaging (MRI) scanner that essentially simultaneously detects blood flow and/or cerebrospinal fluid (CSF) movement in plural slices or slabs of a subject in the scanner, comprising:

a source of radio frequency (RF) excitation pulses configured to apply to the subject, in each phase of a time succession of time periods 1-n, where n is a positive integer greater than unity, one or more RF pulses, wherein:

each RF pulses is a multi-band pulse that includes plural frequency bands selectively offset from each other in frequency and/or phase; and the frequency bands in each of the multi-band pulses essentially simultaneously excite respective plural slices or slabs in the subject, thereby causing the subject to essentially simultaneously emit MRI signals from each of the excited slices or slabs;

a source of magnetic gradients configured to apply to the subject, in a timed relationship relative to each RF pulse:

slice or slab encode magnetic gradients $G_{slice}$ phase encode magnetic gradients $G_{pe}$; and readout magnetic gradients $G_{ro}$;

an antenna configured to acquire the MRI signals emitted from the subject with in timed relationship to the readout magnetic gradients $G_{ro}$;

said scanner being configured to repeat the applying and acquiring steps for said succession of time periods;

said source of magnetic gradients being further configured to apply, in at least some of the phases, one or more bipolar velocity encoding magnetic gradients $G_{venc}$ at one or more selected axes relative to the scanner and in timed relationship with one or more of the RF pulses;

an MRI signal processor configured to computer-process the acquired MRI signals, including velocity dependent phase shifts reflected in the MRI signals, into indications of at least one of blood flow and cerebrospinal fluid (CSF) movement in the slices or slabs; and a display configured to display said indications displaying said indications.

* * * * *